United States Patent [19]

Shimizu et al.

[11] Patent Number: 5,824,339
[45] Date of Patent: Oct. 20, 1998

[54] EFFERVESCENT COMPOSITION AND ITS PRODUCTION

[75] Inventors: Toshihiro Shimizu, Hyogo; Tetsuro Tabata; Junichi Kikuta, both of Osaka, all of Japan

[73] Assignee: Takeda Chemical Industries, Ltd, Osaka, Japan

[21] Appl. No.: 708,663

[22] Filed: Sep. 5, 1996

[30] Foreign Application Priority Data

Sep. 8, 1995 [JP] Japan .................................. 7-257064

[51] Int. Cl.⁶ ............................................. A61K 9/46
[52] U.S. Cl. ..................... 424/466; 424/465; 427/2.14; 427/2.21
[58] Field of Search .................... 424/466, 465; 427/2.14, 2.21

[56] References Cited

U.S. PATENT DOCUMENTS

| | | | |
|---|---|---|---|
| 3,131,123 | 4/1964 | Masqueliar | 424/466 |
| 4,045,563 | 8/1977 | Berntsson et al. | 424/263 |
| 4,255,431 | 3/1981 | Junggren et al. | 424/263 |
| 4,378,975 | 4/1983 | Tomlinson et al. | 51/309 |
| 4,472,409 | 9/1984 | Senn-Bilfinger | 424/263 |
| 4,508,905 | 4/1985 | Junggren et al. | 546/271 |
| 4,628,098 | 12/1986 | Nohara et al. | 546/271 |
| 4,769,456 | 9/1988 | Nohara et al. | 54/9 |
| 4,786,505 | 11/1988 | Lovgren et al. | 424/479 |
| 4,853,230 | 8/1989 | Lovgren et al. | 424/466 |
| 5,045,321 | 9/1991 | Makino et al. | 424/475 |
| 5,045,552 | 9/1991 | Souda et al. | 514/338 |
| 5,312,824 | 5/1994 | Sohda et al. | 514/338 |
| 5,536,735 | 7/1996 | Takechi et al. | 514/338 |

FOREIGN PATENT DOCUMENTS

| | | |
|---|---|---|
| 0196002 | 1/1986 | European Pat. Off. . |
| 0 622 083 | 11/1994 | European Pat. Off. . |
| 452862 | 7/1995 | European Pat. Off. . |
| 0 670 160 | 9/1995 | European Pat. Off. . |
| 5-921918 | 4/1993 | Japan . |
| 5-92918 | 4/1993 | Japan . |
| 93/00886 | 1/1993 | WIPO . |
| 94/21239 | 9/1994 | WIPO . |
| 96/24338 | 8/1996 | WIPO . |

OTHER PUBLICATIONS

Gergely et al., *Chemical Abstracts*, vol. 108,#173564., 1987.
Bengtsson et al., *Chemical Abstracts*, vol. 122,#170234., 1994.
Japanese Abstract of Japan, "Release Control Gel Agent; Comprise Medicine Substance Hydroxypropyl Cellulose Ethanol Soluble Plasticised", Japanese 63–222121, Sep. 16, 1988.
Japanese Abstract of Japan, "Sustained Release Drug Preparation Comprise Drug Solid Coating Aqueous Alcoholic Solution Bind Fine Hydrophobic Solid Particle", Japanese 63–099009, Apr. 30, 1988.
European Abstract of Europe, Honjo et al., "New IGE Bind Factor Protein Obtain Culture Cell Class Specific FC Receptor Surface", European 2–48211, Mar. 1192.
Japanese Abstract of Japan, "Release Control Granule; Contain Medicine Substance Water Soluble High Molecular Substance Ethanol Insoluble Ethanol Soluble", Japanese 63–222112, Sep. 16, 1988.
Japanese Abstract of Japan, "Slow Release Solid Preparation; Contain Pharmaceutical Ingredient Calcium Silicate Hydroxypropyl Methylcellulose", Japanese 63–243036, Oct. 7, 1988.
European Abstract of Europe, Koyama et al., "Produce Core Granule Option Contain Drug; Spray Core Low Substitute Hydroxypropyl Cellulose" European 3–61874, Apr. 4, 1990.
European Abstract of Europe, Kamada, "Sphere Microcrystalline Cellulose Seed Core Forming Sphere Granule Active Ingredient Sustained Release", European 4–52862, Oct. 23, 1991.
Japanese Abstract of Japan, "Nucleus Contain Powder Control Leach Drug Consist Fine Particle Nucleus Coating Water Soluble High Molecular Compound Physiological Active Substance" Japanese 05–092918, Apr. 16, 1993.
Japanese Abstract of Japan, "Fine Crystal Sphere Cellulose Granule; Preparation Granule Apparatus Rotating Fan", Japanese 61–213201, Sep. 22, 1986.
Great Britain Abstract of Great Britain, "Methylthio Benzimidazole Derivative; Treat Gastric Disorder Ulcer Inhibit Gastric Secretion", Great britain 2 134 523, Aug. 15, 1984.
European Abstract of Europe, Fujimoto et al., "New Methylthio Benzimidazole Compound; Useful Gastric Acid Secretion Inhibit Preparation Halomethyl Pyridine Mercapto Benzimidazole", Japanese 2–95603, Dec. 21, 1988.
European Abstract of Europe, Figala et al., "New DI Alkoxy Pyridyl Methyl Thio Benzimidazole Derivative; Inhibit Gastric Acid Secretion Useful Treat Prevent Ulcer", Europe 1–66287, Jan. 2, 1986.
European Abstract of Europe, Dietrich et al., "New Tablet Pellet Oral Administer Improve Stabilised Gastric Fluid Resistance Core Contain Polyvinyl Pyrrolidone Hydroxypropyl Methylcellulose Bind Option Mannitol Fill", Europe 51–9365, Dec. 23, 1992.

*Primary Examiner*—Thurman K. Page
*Attorney, Agent, or Firm*—Foley & Lardner

[57] ABSTRACT

An effervescent composition comprising a core-shell powder consisting of a fine granular core spray-coated with a liquid mixture containing a water-soluble polymer such as hydroxypropylcellulose or hydroxypropylmethylcellulose, and at least one physiologically active substance, especially an acid-sensitive drugs, and enteric coating film, an effervescing component and an auxiliary effervescing agent which provides for controlled release of the physiologically active substance and in useful for preparing uniform solution or suspension having a refreshing sensation on ingestion.

14 Claims, No Drawings

EFFERVESCENT COMPOSITION AND ITS PRODUCTION

FIELD OF THE INVENTION

The present invention relates to an effervescent composition providing for the optimal control of the rate of release of physiologically active substances, which finds application in the food, pharmaceutical, and agrochemical fields and to a method of producing said composition.

BACKGROUND OF THE INVENTION

In general, much research is being done in the field of drug delivery systems (DDS) for foods, medicines, farm chemicals, etc. Particularly among oral dosage forms, granules show no remarkable individual-to-individual variation in gastric emptying rate and absorption rate and are less susceptible to the influence of diets as compared with tablets. Therefore, oral compositions are sometimes provided in the form of granules, in the form of tablets containing granules [Drug Development and Industrial Pharmacy, 9 (7), 1379–1396 (1983)], or in the form of capsules filled with granules.

Referring to granules, JP-A-S63(1988)-222121 discloses a production method which comprises extrusion-molding a drug, hydroxypropylcellulose, and an ethanol-soluble plasticizer to provide granules. In this process, the plasticizer is used in a large amount to provide sufficient plasticity. JP-A-S63(1988)-99009, which corresponds to EPO 248211, discloses a production method such that while drug-containing solid particles are agitated or tumbled, an aqueous or alcohol solution of a binder is sprayed against the particles and, in addition, a hydrophobic solid powder hardly soluble in the gastric and intestinal fluids is dusted on the particles. By this process, long-acting granules can be obtained.

JP-A-S63(1988)-222112 discloses a preparation of a long-acting granular preparation comprising a drug, an ethanol-insoluble, water-soluble polymer, and an ethanol-soluble, water-soluble polymer. To manufacture this preparation, the ethanol-insoluble, water-soluble polymer must be used in a large amount such that the ethanol-insoluble, water-soluble substance is used in a proportion of at least 55% in working examples.

JP-A-S-63(1988)-243036 discloses an intragastric resident long-acting granular preparation containing calcium silicate and hydroxypropylmethylcellulose. In this technology, dry calcium silicate powder is formulated to give an apparent specific gravity of not greater than 1.0.

JP-A-H2(1990)-1749431, which corresponds to EPO 361874, proposes a production which comprises spray-coating core-granules with a dispersion of low-substituted hydroxypropylcellulose to provide core-shell granules. The granules obtained by this process are high in mechanical strength and yet high in disintegratability.

EP 0452862A2 discloses spherical granules comprising inactive spherical cores containing at least 50 weight % of microcrystalline cellulose and having a average particle diameter of 100–1000 $\mu$m coated with an active ingredient-containing powder with the aid of an aqueous binder solution and further spray-coated with an aqueous solution or dispersion of a coating agent.

The granules prepared by those production technologies are invariably characterized in that a large majority of particles have diameters over 500 $\mu$m. The particle diameters of these granules are not only large but are substantially uniform. Therefore, when coated with a release-controlling vehicle for optimizing the release of the active substance, these granules offer the advantage of small variations in coating amount. However, because of their large particle size, these granules are not only poor in prescription characteristics but, when used for tablets or capsules, cause large variations in content. Furthermore, when provided in granular form, the particle size test and disintegration test are essential under the Pharmacopoeia of Japan XI (hereinafter sometimes referred as JP), General Rules, 5. Granules, and it is difficult to design a controlled release formulations satisfying the test requirements.

On the other hand, JP does not specify for a disintegration test for powders. Moreover, because their particle size is not greater than 500 $\mu$m, powders are better compoundable than granules and, when processed into tablets and capsules, cause a smaller variation in content. Furthermore, powders are generally higher than granules in gastric emptying rate and absorption rate. However, because of this high gastric emptying rate, powders may cause an early rise in blood concentration depending on drugs, thus leading to development of side effects. Furthermore, when the method, among the above-mentioned prior art technologies relating to granules, which comprises incorporating a drug in the core phase and controlling the release of the substance by means of a polymeric carrier coating is applied as it is to powders, a large variation in content, poor coating accuracy, and an increased coating amount are inevitable. Thus, as far as powders are concerned, the release of drug can hardly be controlled with precision because of their relatively small particle size compared with granules.

JP-A-H5(1933)-92918 proposes a technology for producing core-shell powders having particle diameters substantially not larger than 500 $\mu$m which comprises coating fine granular cores with at least one kind of physiologically active substance and a water-soluble polymer. The core-shell powders thus obtained have the advantage that even through they are of small particle size, the release of the bioactive substance can be controlled with comparatively high precision.

Referring to the effervescent pharmaceutical preparations, it has been possible only with difficulty to incorporate acid-sensitive drugs in stable form into effervescent tablets of effervescent instant granular products, since in contact with the acid of the effervescent system such compositions hydrolyze or decompose, i.e. they are not shelf-stable. Furthermore, whenever such a substance also affects the surface tension of water, hydrophobic particles of the drug tend to creep upward on the glass or deposit at the bottom of the glass. On the other hand, in certain cases, the antacid side-effect of an effervescent tablet is undesirable for many drugs. To provide an effervescent system which will avoid the aforesaid disadvantages and offer the possibility of administering to a patient pharmaceutical substances in pleasant-to-drink effervescent solutions, EP0670160A1 proposes a granular effervescent product suitable for preparing an aqueous solution or suspension of one or more pharmaceutically active substances, especially acid-sensitive drugs such as for example, beta carotene, cimetidine, ranitidin or cisapride, for oral administration. This product comprises effervescent grains obtained from carrier crystals of at least one solid, edible organic acid which are substantially covered by at least one coating containing at least one water-soluble neutral substance, wherein said neutral substance is effective for depressing the melting point of the acid crystals on their surface, and at least one substance selected from the group consisting of alkali carbonate, alkali bicarbonate, alkaline earth carbonate, alkaline earth bicarbonate, alkali salt of at least one solid edible organic acid, and alkaline earth salt of at least one solid edible organic acid is applied onto said coating.

SUMMARY OF THE INVENTION

The object of the present invention is to provide a powder composition capable of physiologically active for accurate control of the rate of release of a bioactive substance despite its small particle size and a method for its production, as well as a pharmaceutical preparation containing said powder composition such as a granule, tablet, or capsule.

Another object of the present invention is to provide an effervescent composition which, when dispersed in water, provides for substantially the same rate of release of a physiologically active substance, especially an acid-sensitive pharmaceuticals as that after administration of the same substance alone. The preferable embodiment of the effervescent composition is one which is suitable for preparing an uniform suspension of an acid-sensitive active substance for oral administration.

To solve the aforesaid problems, the inventors of the present invention did much research and found core-shell powders with a minimum of variation in coating amount and an increased content of an active substance, which are obtained by spraying small-diameter cores with a liquid mixture of a water-soluble polymer and the active substance to provide an drug-containing shell layer, whereby there can be properly controlled the release of the active substance in combination with an effervescing component. Further, a refreshing sensation on ingestion can be imparted by using the core-shell powders and the effervescent component in combination. The present invention has been developed on the basis of the above findings.

That is, the present invention relates to an effervescent composition which comprises (a) a core-shell powder which essentially consists of fine granular core having a specific volume not exceeding 5 ml/g coated with a layer comprising a water-soluble polymer and an effective amount of an acid-sensitive physiologically active substance and an enteric coating layer, wherein the average particle diameters of the core-shell powder is not exceeding about 300 μm;

(b) an effervescing component; and (c) an auxiliary effervescing agent; wherein the proportion of (c) is from about 1.0 to about 2.0 equivalents relative to (b).

According to the production method of the present invention, an effervescent core-shell powder composition is produced by admixing said core-shell powders with said effervescing component and effervescing agent of separate particles.

DETAILED DESCRIPTION OF THE INVENTION

Throughout this specification, the term "coating" or "coated" means not only a complete coverage of the core but also a partial coverage of the core as well as adsorption on the surface of the core or adsorption into the core.

The term "spherical" as used herein is not only synonymous with globose but broadly synonymous with ellipsoidal, pyriform, tear drop-shaped, etc., which can be defined by curved planes.

The average diameter of the fine granular cores is not exceeding about 250 μm and may be about 50–250 μm, preferably about 100–250 μm. As cores having diameters within the above range, the particle should pass through #50 (300 μm) sieve, and not more than about 5 w/w % of them may remain on #60 (250 μm) sieve and not more than about 10 w/w % of them may pass through #282 (53 μm) sieve.

The specific volume of the fine granular cores is not more than about 5 ml/g, preferably not more than 3 ml/g. Examples of the fine granular cores includes crystalline cellulose beads of the size range about 150–250 μm (Avicel SP, Asahi Chemical Industry Co., Ltd.; hereinafter referred to as Avicel SP), crystalline cellulose-lactose beads [about 150–250 μm beads composed of crystalline cellulose (3 parts) and lactose (7 parts) (Nonpareil, Freund Industries; hereinafter referred to as NP-7:3), about 150–250 μm beads composed of crystalline cellulose (5 parts) and lactose (5 parts) (Nonpareill, Freund Industries; hereinafter referred to as NP-5:5 etc.), about 50–250 μm beads composed of lactose (9 parts) and Pregelatinized starch (1 part) as manufactured by agitation-granulation, a fraction of granules up to 250 μm in diameter among microcrystalline cellulose beads as described in JP-A-S61(1987)-213201, wax or other beads obtainable by spray-chilling or melt-granulation, oil fraction-gelatin or other beads, porous granules made of calcium silicate, starch, chitin, cellulose, chitosan, etc., sucrose, crystalline lactose, crystalline cellulose, sodium chloride, etc., either in bulk form or in processed form. Further, the core may be prepared in a desired particle size by known pulverization or granulation using the foregoing substance and sieving the resulting granules.

The above-mentioned core may contain any of the drugs to be mentioned hereinafter but since the release of the drug is controlled by the drug-containing coating-layer, the core need not contain the drug.

There is no particular limitation on core morphology. It may for example be a fine granule or, in order to reduce the variation in coating amount and increase the coating amount, it is preferably spherical.

The water-soluble polymer that can be used includes ethanol-soluble, water-soluble polymers [e.g. cellulose derivatives such as hydroxypropylcellulose (hereinafter referred to as HPC), polyvinylpyrrolidone, etc.] and ethanol-insoluble, water-soluble polymers [e.g. cellulose derivatives such as hydroxypropylmethylcellulose (hereinafter referred to as HPMC), methylcellulose, carboxymethylcellulose sodium, etc., sodium polyacrylate, polyvinyl alcohol, sodium alginate, guar gum, etc.]. The release rate of the physiologically active substance can be controlled by using an ethanol-soluble, water-soluble polymer in combination with an ethanol-insoluble, water-soluble polymer or using a plurality of water-soluble polymers differing in viscosity.

The preferred water-soluble polymer includes cellulose derivatives such as HPC, HPMC, methyl-cellulose, etc., and polyvinyl alcohol. Particularly preferred are cellulose derivatives such as HPC and HPMC.

HPC contains 53.4–77.5 weight % of hydroxypropoxy groups. The preferred content is 60–70 weight %. A 2 weight % aqueous solution of HPC at 20° C. is generally about 1–150000 cps (centipoise). As a typical grade of HPC, JP (Japanese Pharmacopoeia) hydroxypropylcellulose can be mentioned. The viscosity values of HPC mentioned below are the values determined using 2 weight % aqueous solutions at 20° C. The HPC for use in the present invention is different from the low-substituted hydroxypropylcellulose mentioned in said JP-A-H2(1990)-174931 in the degree of hydroxypropoxy group.

HPMC is a mixed ether containing both methoxy and hydroxypropoxy groups. The methoxy content of HPMC may be about 19–30 weight % and the hydroxypropoxy content thereof may be about 4–12 weight %. The viscosity of a 2 weight % aqueous solution of HPMC at 20° C. is generally about 1–40000 centistokes. As HPMC of this grade, JP hydroxypropylmethylcellulose 2208, JP hydroxypropylmethylcellulose 2906, and JP hydroxypropylmethylcellulose 2910, among others, can be used. These hydroxypropylmethylcellulose can be used independently or as a mixture.

The physiologically active substances that can be used in the invention includes a variety of drugs which are employed in the fields of food, medicine, agriculture, etc., only provided it can be administered orally. The preferred physiologically active substance includes but is not limited to the following medicinally active substances: central nervous system drugs (diazepam, idebenone, aspirin, ibuprofen, paracetamol, naproxen, piroxicam, diclofenac, indomethacin, sulindac, lorazepam, nitrazepam, phenytoin, acetaminophan, ethenzamide, ketoprofen, etc.), cardiovascular system drugs (molsidomine, vinpocetine, delapril hydrochloride, propranolol, methyldopa, dipyridamole, furosemide, triamterene, nifedipine, atenolol, spironolactone, metoprolol, pindolol, captopril, isosorbide dinitrate, etc.), respiratory system drugs (amlexanox, dextromethorphan, theophylline, pseudoephedrine, salbutamol, guaifenesin, etc.), gastrointestinal system drugs (benzimidazole drugs such as lansoprazole, omeprazole, etc., cimetidine, ranitidine, panoreatin, bisacodyl, 5-aminosalicylic acid, etc.), antibiotics and chemotherapeutic agents (cefalexin, cefaclor, cefradine, amoxicillin, pivampicillin, bacampicillin, dicloxacillin, erythromycin, erythromycin stearate, lincomycin, doxycycline, sulfamethoxazole-trimethoprim, etc.), metabolic system drugs (serrapeptase, lysozyme chloride, adenosine triphosphate, glibenclamide, potassium chloride, etc.), vitamins (vitamin $B_1$, vitamin $B_2$, vitamin $B_6$, vitamin C, fursultiamine, vitamin A, vitamin E, vitamin D, vitamin K, etc.), and antacids. These drugs can be used independently or in combination. Among the others, an acid-sensitive medicament which may unstable and/or inactivated with acid, such as vitamins (vitamin $B_{12}$, Vitamin C, fursultiamine, folic acid, vitamin $B_{12}$, Vitamin A, vitamin D or like), peptide drugs such as, enzymes (serrapeptase etc), antibiotics, cimetidine, ranitidine, known benzimidazole drugs having antiulcer activity, represented by the formula:

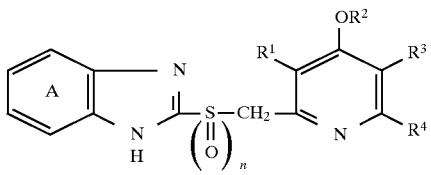

wherein ring A may optionally be substituted, $R^1$, $R^3$, and $R^4$, which are the same or different, are hydrogen, an alkyl group or an alkoxy group; $R^2$ is a $C_{1-4}$ alkyl group which may optionally substituted with halogen, hydroxy or $C_{1-4}$ alkoxy groups; and n is 0 or 1; or a salt thereof, such as lansoprazole or omeprazole are preferably used.

Referring to the above formula, the substituent on ring A includes halogen, $C_{1-10}$ alkyl, $C_{3-7}$ cycloalkyl, $C_{2-16}$ alkenyl or $C_{1-10}$ alkoxy group which may be substituted, cyano, carboxy, carbalkoxy, carbalkoxyalkyl, carbamoyl, carbamoylalkyl, hydroxy, hydroxyalkyl, acyl, carbamoyloxy, nitro, acyloxy, aryl, aryloxy, alkylthio and alkylsulfinyl, among others.

The alkyl group represented by $R^1$, $R^3$ or $R^4$ includes $C_{1-10}$ straight-chain or branched alkyl groups. Among such alkyl groups are methyl, ethyl, n-propyl, isopropyl, n-butyl, isobutyl, sec-butyl, tert-butyl, n-pentyl, isopentyl, neopentyl, hexyl, heptyl, octyl, nonyl, decyl and so on. Among others, $C_{1-5}$ straight-chain or branched alkyl groups are particularly desirable.

The alkoxy group represented by $R^1$, $R^3$ or $R^4$ includes $C_{1-10}$ alkoxy groups. Among such alkoxy groups are methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred groups are $C_{1-6}$ alkoxy groups. The more desirable are $C_{1-3}$ alkoxy groups.

The alkyl group represented by $R^2$ and the alkoxy group used as substituent thereof may includes the above exemplified $C_{1-4}$ alkyl and $C_{1-4}$ alkoxy groups. The number of substituents is preferably 1 to 3.

These compounds are described in, for example. U.S. Pat. Nos. 4,045,563, 4,255,431, 4,359,465, 4,472,409, 4,508,905, JP-A-59 181277, U.S. Pat. Nos. 4,628,098, 4,378,975, 5,045,321, 4,786,505, 4,853,230, 4,769,456, 5,045,552, 5,536,735, EP-A-295603, U.S. Pat. Nos. 5,312,824, EP-A-166287 and EP-A-519365, etc.

The benzimidazole drugs are the most preferable physiologically active substance.

Thus, the preferable embodiment of the core-shell powder of the invention is a powder consisting of a fine granular core coated with a layer (shell-layer) comprising a water-soluble polymer and an effective amount of an acid-sensitive pharmaceutically active drug and an enteric-coating layer (shell-layer).

For increased strength of the core-shell powders, the drug-containing layer may contain various additives inclusive of the low-substituted hydroxypropylcellulose (hereinafter referred to as L-HPC) described in JP-A-H2 (1990)-174931.

The additives mentioned above may be the substances usually added in the production of powders. Thus, various excipients such as lactose, corn starch, sucrose, talc, crystalline cellulose, mannitol, light silicic anhydride, magnesium carbonate, calcium carbonate, L-cysteine, etc.; binders such as pregelatinized starch, partially pregelatinized starch, methylcellulose, carboxymethylcellulose, polyvinylpyrrolidone, pullulan, dextrin, gum arabic, etc.; disintegrators such as carboxymethylcellulose calcium, starches, crosslinked carboxymethylcellulose sodium, crosslinked insoluble polyvinylpyrrolidone, etc.; and coloring agents such as titanium dioxide, red iron oxide, tar pigment, etc. can be mentioned. Stabilizer may preferably added for stabilizing the shell-unstable drugs as the additives. More than one species each of such additives can be employed.

The proportion of the water-soluble polymer such as HPC and/or HPMC may only be within the range capable of controlling the release of a drug contained in the core-shell powders. Based on the total weight of the whole core-shell powders, the proportion may for example be from or about 0.1 to or about 50 weight % and preferably from or about 1 to or about 30 weight %. If the proportion of the water-soluble polymer is smaller than about 0.1 weight %, it will be difficult to control the release of the drug, while the use of said polymer in excess of about 50 weight % results in a reduced drug content.

The proportion of the coating-layer with respect to the core can be liberally selected within the range permitting control of the release of the drug and may for example be from or about 50 to or about 400 parts by weight based on 100 parts by weight of the core. If the proportion of the coating-layer is smaller than about 50 parts by weight, the release of the active substance can hardly be controlled. On the other hand, if the limit of about 400 parts by weight is exceeded, there will occur a marked growth of particles to cause more deviations from the particle size specification of the powders.

The coating may be comprised of a single layer or consist of a plurality of layers and it is sufficient that the bioactive substance be contained in at least one coating-layer. The plurality of coating-layers may consist of the layers such as an undercoat layer, an inactive layer and an enteric layer in any combination.

For the purpose of protecting an acid-sensitive drug or insuring dissolution in the intestinal fluid, the core-shell powders should be coated with an enteric coating. The enteric-coating agent that can be used for such purposes includes but is not limited to cellulose acetate phthalate (CAP), hydroxypropylmethylcellulose phthalate (hereinafter referred to as HP-55), hydroxymethylcellulose acetate succinate, acrylic copolymers (e.g. Eudragit L30D-55), carboxymethylethylcellulose and shellac.

The proportion of the enteric-coating layer may be selected within the range of from or about 35 weight % to or about 50 weight % based on the total amount of the enteric core-shell powder. If the portion of the enteric coating layer is smaller than about 35%, the acid sensitive drug can be unstable is a gastric fluid. On the other hand if the portion of enteric coating layer exceeds about 50%, the release of the active substance would be decreased.

The average particle diameter of the core-shell powder is not larger than about 300 $\mu$m, preferably in the range of from or about 100 to or about 300 $\mu$m, and for still better results, in the range of about 150–300 $\mu$m. As the core-shell powder having a diameter within the range, the granule of the powder should pass through a sieve of 400 $\mu$m screen, and not more than about 5 w/w % of the total amount of the powder may remain in a #42 (355 $\mu$m) sieve and not more than about 5 w/w % thereof may pass through #100 (150 $\mu$m) sieve. For effervescent use, smaller size of particles is advantageous for rapidly preparing a uniform solution or suspension and keeping there uniformity. However, if the particle size is too small, there tends to occur the trouble that in the course of production the powders are attracted to the equipment walls by static electricity.

The specific volume of the core-shell powder is not exceeding about 3 ml/g, preferably not exceeding 2 ml/g. For insuring a stable uniformity in the effervescent solution, the specific volume of the core-shell powder is preferably selected in accordance with that of the solution.

The release rate of the drug in the core-shell powders can be controlled by using a plurality of the water-soluble polymer (e.g. HPC, HPMC, etc.) solutions varying in viscosity or content or modifying the ratio of an ethanol-soluble, water-soluble polymer (e.g. HPC) to an ethanol-insoluble, water-soluble polymer (e.g. HPMC). Further, the release of drug can also be controlled without being much influenced by the pH of the environment in which they are released.

The effervescent composition of the present invention contains an effervescing component for providing a refreshing sensation or ingestion. With this effervescent dosage form, the release of a physiologically active ingredient can be accurately controlled as it is the case with the core-shell powders as such. As the effervescing component, a variety of substances can be utilized unless the safety of the composition is compromised. To mention a few examples, alkali metal carbonates (e.g. sodium carbonate, potassium carbonate, etc.), alkali metal hydrogen carbonates (e.g. sodium hydrogen carbonate, potassium hydrogen carbonate, etc.), and ammonium carbonate can be employed. These effervescing agents can be used singly or in combination. Among preferred effervescing agents are sodium carbonate, sodium hydrogen carbonate, and ammonium carbonate. The proportion of the effervescing component can be selected from the range providing the required effervescence and, based on 100 parts by weight of the core-shell powders, may for example be from about 10 to about 2500 parts by weight, preferably about 50–2000 parts by weight (e.g. 75–1500 parts by weight), or for still better results, about 100–1000 parts by weight.

The effervescing component mentioned above can be used either independently or in combination with an auxiliary effervescing agent. The auxiliary effervescing agent includes a variety of edible organic acids, typically hydroxy-carboxylic acids such as citric acid, tartaric acid, malic acid, lactic acid, gluconic acid, etc., saturated aliphatic carboxylic acids such as acetic acid, succinic acid, etc., and unsaturated aliphatic carboxylic acids such as fumaric acid. These auxiliary effervescing agents can also be used singly or in combination. Among preferred edible auxiliary effervescing agents are hydroxy-carboxylic acids such as citric acid and tartaric acid. The proportion of the auxiliary effervescing agent is generally about 0.1–2.0 equivalents and preferably about 0.3–1.7 equivalents based on said effervescing component. The proportion of the auxiliary effervescing agent for enteric-coated core-shell powders should be about 1.0–2.0 equivalents and preferably about 1.3–1.7 equivalents relative to the effervescing component in order that the pH of the system may be maintained on the acidic side, while the proportion for gastric fluid soluble core-shell powders should be about 0.1–1.0 equivalent and preferably about 0.3–0.7 equivalents, in order that the system pH of the composition may be maintained on the alkaline side.

The effervescent composition of the present invention need only contain said core-shell powders and said effervescing component but may further contain said additives (e.g. excipients, binders, disintegrants, etc.) where necessary.

The effervescent composition of the present invention can be manufactured by coating said fine granular cores with a liquid mixture containing a water-soluble polymer and at least one physiologically active substance to give core-shell powders and mixing the core-shell powders with said effervescing component. The auxiliary effervescing agent may preferably contained in said mixture.

The liquid mixture mentioned above may be a solution or a dispersion. The liquid mixture can be prepared by using water, an organic solvent such as ethanol, or a mixture thereof.

The concentration of said water-soluble polymer in the liquid mixture should vary with the formulating amounts of the drug and additives but is generally from or about 0.1 to or about 50 weight % and preferably about 0.5–10 weight %. If the concentration is less than about 0.1 weight %, the drug will not be well immobilized on the core granules. If the limit of about 50 weight % is exceeded, the viscosity of the liquid mixture will be too high to provide practically acceptable workability.

The coating-layer is not limited to a single layer but may be made up of a plurality of layers. Thus, one may select the optimum formulating amount and viscosity grade for the water-soluble polymer and/or apply successive coats using liquid mixtures varying in the concentrations of the drug and additives to thereby create a continual or stepwise gradation in the distribution of the drug in the shell. In this connection, insofar as the whole coating-layer contains from about 0.1 to or about 50 weight % of the water-soluble polymer, liquid mixtures deviating from the above concentration range of from or about 0.1 to or about 50 weight % may be employed. Furthermore, an inert film may be interposed between layers by known technology to isolate the drug containing layers from each other.

In the event two or more physiologically active substances which are hardly compoundable are employed, the fine granular core may be coated with liquid mixtures containing such drug respectively either concurrently or in a sequence.

As an alternative production process according to the present invention, core-shell powders can be manufactured by spraying a fine granular core with said liquid mixture and simultaneously dusting a dusting powder containing the drug and/or additives over the cores. In this process, the required shell can be provided by the simple procedure of dusting a dusting powder. The particle size of such a dusting powder is preferably not greater than about 50 $\mu$m.

The granulation process comprising coating the fine granular core with said liquid mixture in the above manner. The granulation temperature should be within the range not adversely affecting the stability of the drug. Where the stability of the drug is good, the temperature of the liquid mixture need not be carefully controlled. Generally, the temperature of the liquid mixture may be equal to the room temperature (e.g. about 1°–30° C.). There is no particular limitation on the method of covering the core. For example, the centrifugal fluidized coating granulator, fluidized coating granulator, agitation-granulator, or any other routine granulation equipment can be employed. As specific models of centrifugal fluidized coating granulator, there can be mentioned "CF apparatus" and "Spira-flow" available from Freund Industries, "Multiplex" from Powrex, and "New-Marume" from Fuji Paudal can be mentioned. The method of spray coating with said liquid mixture can be selected according to the type of available granulation equipment. Thus, for example, any of bottom spray, tangential spray and other coating modes can be selectively employed.

The granulation thus obtained is dried and sieved to provide core-shell powders uniform in particle size. Since the shape of powders generally corresponds to the shape of the fine granular cores used, even truly spherical core-shell powders can be successfully obtained. As the sieve, a 50-mask (300 $\mu$m) circular sieve, for instance, can be used and by collecting particles passing through such a sieve, the desired core-shell powders can be obtained.

For the purpose of masking the taste or insuring dissolution in the intestinal fluid or in the gastric fluid, the core-shell powders obtained as above may be further coated in the routine manner.

The coating agent that can be used for such purposes includes but is not limited to HPMC, ethylcellulose, hydroxymethylcellulose, hydroxypropylcellulose, polyoxyethylene glycol (e.g. Macrogel 6000), Tween 80, Pluronic F68, castor oil, cellulose acetate phthalate, hydroxypropylmethylcellulose phthalate (hereinafter referred to as HP-55), hydroxymethylcellulose acetate succinate, acrylic copolymers (e.g. Eudragit L30D-55), carboxymethylethylcellulose, poly vinyl acetal diethylaminoacetate, shellac, wax, talc, titanium dioxide, and red iron oxide.

If desired, a plurality of coating-layers (e.g. an HPMC undercoat layer, an acrylic copolymer or other enteric or gastric fluid soluble layer) may be formed on the core-shell powders using a plurality of coating compositions.

The effervescent composition obtained by mixing said core-shell powders with said effervescing agent can be used directly as an effervescent dosage form. The composition can be further formulated with said additives such as an excipient, binder, disintegratant, etc. and granulated or compressed to provide granules or tablets. The core-shell powder of the invention may be filled into capsule shells to provide capsules in addition to these dosage forms.

Since the effervescent composition of the present invention contains the core-shell powders described above, it lends itself well to compounding with a minimum of variation in content. Moreover, since it contains an effervescing component in addition to core-shell powders, the release rate of the drug can be accurately controlled despite the small particle diameter. In addition, the composition provides an uniform effervescent solution of acid-sensitive drugs with a refreshing sensation on ingestion.

Thus, in accordance with the present invention, compositions having the above useful characteristics can be easily obtained by the expedient procedure of mixing core-shell powders with an effervescing agent.

EXAMPLES

The following examples are merely intended to illustrate the present invention in further detail and should by no means be construed as defining the scope of the invention.

Example 1
Production of Core-Shell Powders

A centrifugal fluidized coating granulator (Powrex, MP=10) was charged with 800 g of Avicel SP (particle diameter=100–200 $\mu$m) and with the inlet air temperature and the temperature of the load being controlled at 80° C. and about 38° C., respectively, a bulk liquid of the following composition was coated on the Avicel by the tangential spray method. The spraying operation was stopped when the specified amount of the bulk liquid had been delivered and the load was dried in the granulator for 5 minutes. The resulting granules were sieved through a #60 circular sieve (250 $\mu$m) and a #100 circular sieve (150 $\mu$m) to provide 1450 g of core-shell powders.

[Bulk Liquid Composition]

Lansoprazole 300 g

Magnesium carbonate 200 g

L-HPC 50 g

Talc 50 g

HPC (Type SSL) 100 g

Water 3200 g

Production of an Undercoated Core-Shell Powder

The same fluidized coating granulator as above (MP-10) was charged with 1200 g of the above core-shell powders and with the inlet air temperature and the load temperature being controlled at 85° C. and about 40° C., respectively, a undercoating liquid of the following composition was applied by the tangential spray method at a spray rate of 12 g/min, to provide film-undercoated core-shell powders.

[Undercoating Liquid]

HPMC (Type 2910, viscosity=3 centistokes) 80 g

Water 1520 g

Production of Enteric-Coated Core-Shell Powder

The same fluidized coating granulator as above (MP-10) was charged with 960 g of the above undercoated core-shell powders and with the inlet air temperature and the load temperature being controlled at 65° C. and about 38° C., respectively, an enteric film-coating liquid of the following composition was applied by the tangential spray method at a spray rate of 15 g/min. The coated powders were dried in vacuum oven at 40° C. for 16 hours and sieved through a #42 circular sieve (355 μm) and a #80 circular sieve (177 μm) to provide 1500 g of enteric-coated core-shell powders.

[Enteric Film Coating Composition]

Eudragit L30D-55 1783.8 g

Talc 160.8 g

Macrogol 6000 52.8 g

Titanium dioxide 52.8 g

Polysorbate 80 24.0 g

Water 3744.0 g

To eliminate static charge, a tumbling-mixer (TM-15, Showa Chemical) was charged with 1500 g of the above enteric-coated core-shell powders, 6 g of talc, and 6 g of light silicic anhydride and the load was mixed at 30 rpm for 3 minutes. The resulting enteric-coated core-shell powders showed a sharp particle size distribution meeting the requirements of the JP particle size test.

| Sieve | Weight ratio |
|---|---|
| residued on #18 (850 μm) sieve | 0% |
| residued on #30 (500 μm) sieve | 0% |
| residued on #200 (75 μm) sieve | 100% |
| passed through #200 (75 μm) sieve | 0% |

Example 2
Production of an Effervescent Composition

An effervescent composition was produced by mixing 300 mg of the enteric-coated core-shell powders obtained in Example 1, 1800 mg of citric acid powder, and 900 mg of sodium hydrogen carbonate powder.

Example 3
Production of Core-Shell Powders

A centrifugal fluidized coating granulator (Powrex, MP-10) was charged with 800 g of Avicel SP (particle diameter=100–200 μm) and with the inlet air temperature and the load temperature being controlled at 80° C. and about 38° C., respectively, a bulk liquid composition prepared according to the following recipe was applied by the tangential spray method. The spraying operation was stopped when the specified amount of the bulk liquid composition had been sprayed and the load was dried in the granulator for 5 minutes. The resulting granules were sieved through a #60 circular sieve (250 μm) and a #100 circular sieve (150 μm) to provide 1450 g of core-shell powders.

[Bulk Liquid Composition]

Lansoprazole 300 g

Magnesium carbonate 300 g

L-HPC 50 g

Talc 50 g

HPC (Type SSL) 100 g

Water 3200 g

Production of Enteric-Coated Core-Shell Powders

The same fluidized coating granulator as above (MP-10) was charged with 960 g of the above core-shell powders and with the inlet air temperature and the load temperature being controlled at 65° C. and about 38° C., respectively, an enteric film coating composition prepared according to the following recipe was applied by the tangential spray method at a spray rate of 15 g/min. The coated powders were dried in vacuum oven at 40° C. for 16 hours and sieved through a #42 (355 μm) circular sieve and a #80 (177 μm) circular sieve to provide 1500 g of an enteric film-coated core-shell powders.

[Enteric Film Coating Composition]

Eudragit L30D-55 1783.8 g

Talc 160.8 g

Macrogol 6000 52.8 g

Titanium dioxide 52.8 g

Polysorbate 80 24.0 g

Water 3744.0 g

To eliminate static charge, a tumbling-mixer (TM-15, Showa Chemical) was charged with 1500 g of the above enteric-coated core-shell powders, 6 g of talc, and 6 g of light silicic anhydride and the load was agitated at 30 rpm for 3 minutes. The resulting enteric-coated core-shell powders satisfied the requirements of the JP particle size test.

| Sieve | Weight ratio |
|---|---|
| residued on #18 (850 μm) sieve | 0% |
| residued on #30 (500 μm) sieve | 0% |
| residued on #200 (75 μm) sieve | 100% |
| passed through #200 (75 μm) sieve | 0% |

Example 4
Production of a Effervescent Composition

An effervescent composition was produced by mixing 300 mg of the enteric-coated core-shell powders obtained in Example 3, 1800 mg of citric acid powder, and 900 mg of sodium hydrogen carbonate powder.

Test Example 1

The release characteristics of the enteric-coated core-shell powders obtained in Examples 1 and 3 and the effervescent compositions obtained in Examples 2 and 4 were evaluated by JP Dissolution Test, No. 2 Method (150 rpm). Since the test materials were enteric powders, the test was performed by using JP with the 1st fluid and then using the 2nd fluid. The effervescent compositions were respectively dispersed in 100 ml of purified water for the development of effervescence and allowed to stand for 5 minutes prior to testing. The test results are shown in Table 1.

TABLE 1

| Test fluid | the 1st fluid | the 2nd fluid | | |
|---|---|---|---|---|
| Release time | 60 min. | 20 min. | 40 min. | 60 min. |
| Example 1 Enteric-coated core-shell powders | 0% | 90% | 95% | 95% |
| Example 2 Effervescent composition | 0% | 90% | 95% | 95% |
| Example 3 Enteric-coated core-shell powders | 0% | 90% | 95% | 95% |
| Example 4 Effervescent composition | 0% | 90% | 95% | 95% |

It will be apparent from Table 1 that the two enteric-coated core-shell powders are equivalent in acid resistance and drug release rate and that even when an effervescing component is formulated for effervescence and the formulation administered, the powders still show virtually the same acid resistance and drug release rate, thus providing the efficacy equivalent to that of fine granules.

Test Example 2

The specific volume of Avicel SP, the core substance, the core-shell powder, undercoated core-shell powder, and the enteric-coated core-shell powder prepared in Example 1 were determined as in the following volume test.

50 g each of the powders were weighed and transferred gradually to a 200-ml measuring cylinder respectively, and allowed to stand. The specific volume was calculated by dividing the thus measured volume by weight.

The results are shown in Table 2.

TABLE 2

|  | Avicel SP | core-shell powder | undercoated core-shell powder | enteric film coated core-powder |
|---|---|---|---|---|
| Specific volume (ml/g) | 1.22 | 1.24 | 1.20 | 1.16 |

What is claimed is:

1. An effervescent composition which comprises
   (a) a core-shell powder which comprises a fine granular core having a specific volume not exceeding about 5 ml/g coated with a layer comprising a water-soluble polymer and an effective amount of an acid-sensitive physiologically active substance and an enteric coating layer, wherein the average particle diameters of the core-shell powder do not exceed about 300 μm;
   (b) an effervescing component; and
   (c) an auxiliary effervescing agent; wherein the proportion of (c) is from about 1.0 to about 2.0 equivalents relative to (b).

2. The effervescent composition as claimed in claim 1, wherein said fine granular core is physiologically inactive.

3. The effervescent composition as claimed in claim 1, wherein said fine granular core is spherical.

4. The effervescent composition as claimed in claim 1, wherein said water-soluble polymer is a cellulose derivative.

5. The effervescent composition as claimed in claim 1, wherein the proportion of said water-soluble polymer is from or about 0.1 to or about 50% by weight of the core-shell powder.

6. The effervescent composition as claimed in claim 1, wherein said acid-sensitive physiologically active substance is a benzimidazole derivative.

7. The effervescent composition as claimed in claim 6, wherein said benzimidazole derivative is lansoprazole.

8. The effervescent composition as claimed in claim 1, wherein the proportion of said enteric coating layer is about 35 to about 50% by weight of the core-shell powder.

9. The effervescent composition as claimed in claim 1, wherein said effervescing component is at least one member selected from the group consisting of alkali metal carbonates, alkali metal hydrogen carbonates and ammonium carbonates.

10. The effervescent composition as claimed in claim 1, wherein said auxiliary effervescing agent is an edible organic acid selected from the group consisting of hydroxy-carboxylic acids and saturated or unsaturated aliphatic carboxylic acids.

11. The effervescent composition as claimed in claim 1, which contains said effervescing component in a portion of about 10 to about 2500 parts by weight with respect to 100 parts by weight of said core-shell powder.

12. The effervescent composition as claimed in claim 1, which comprises
   (a) a core-shell powder which comprises a physiologically inactive fine granular core coated with a layer comprising a water-soluble cellulose derivative and an effective amount of lansoprazole and an enteric coating layer;
   (b) an effervescing component selected from alkali metal carbonates; and
   (c) an auxiliary effervescing agent selected from edible hydroxy-carboxylic acids; wherein the proportion of (b) is about 100 to about 1000 parts by weight with respect to 100 parts by weight of to (a), and the proportion of (c) is about 1.0 to about 2.0 equivalents relative to (b).

13. A method of producing an effervescing composition which comprises mixing (a) a core-shell powder which comprises a fine granular core having specific volume not exceeding about 5 ml/g coated with a layer comprising a water-soluble polymer and an effective amount of acid-sensitive physiologically active substance and an enteric-coating layer, wherein the average particle diameters of the core-shell powder do not exceed about 300 μm; with
   (b) an effervescing component; and
   (c) an auxiliary effervescing agent; wherein the proportion of (c) is about 1.0 to about 2.0 equivalents relative to (b).

14. An effervescent composition suitable for preparing an aqueous solution or suspension of an acid-sensitive physiologically active substance for oral administration which comprises
   (a) a core-shell powder which comprises a fine granular core having a specific volume not exceeding 5 ml/g coated with a layer comprising a water-soluble polymer and an effective amount of acid-sensitive physiologically active substance and an enteric-coating layer, wherein the average particle diameters of the core-shell powder to not exceeding about 300 μm;
   (b) an effervescing component; and
   (c) an auxiliary effervescing agent; wherein the proportion of (c) is about 1.0 to about 2.0 equivalents relative to (b).

* * * * *